(12) United States Patent
Gold (10) Patent No.: US 7,716,071 B2
(45) Date of Patent: May 11, 2010

(54) SYSTEM AND METHOD FOR MANAGING A PATIENT WITH CHRONIC DISEASE

(76) Inventor: Liana Gold, c/o Alan Levy, 2465 NE. 209 Ter., Aventura, FL (US) 33180

( * ) Notice: Subject to any disclaimer, the term of this patent is extended or adjusted under 35 U.S.C. 154(b) by 1099 days.

(21) Appl. No.: 11/243,254

(22) Filed: Oct. 4, 2005

(65) Prior Publication Data

US 2006/0085225 A1 Apr. 20, 2006

Related U.S. Application Data

(60) Provisional application No. 60/615,666, filed on Oct. 4, 2004.

(51) Int. Cl.
G06F 19/00 (2006.01)
(52) U.S. Cl. .................. 705/3; 705/2; 600/300
(58) Field of Classification Search ......... 705/2, 705/3; 600/300
See application file for complete search history.

(56) References Cited

U.S. PATENT DOCUMENTS

| | | | |
|---|---|---|---|
| 6,028,601 A * | 2/2000 | Machiraju et al. .......... 715/705 |
| 6,589,169 B1 * | 7/2003 | Surwit et al. ................ 600/300 |
| 6,770,029 B2 * | 8/2004 | Iliff ........................... 600/300 |
| 2003/0036923 A1 * | 2/2003 | Waldon et al. ................ 705/2 |
| 2003/0171659 A1 * | 9/2003 | Dean ........................ 600/300 |
| 2004/0210458 A1 * | 10/2004 | Evans et al. .................... 705/2 |

* cited by examiner

Primary Examiner—Gerald J. O'Connor
Assistant Examiner—Lena Najarian
(74) Attorney, Agent, or Firm—The Belles Group, P.C.

(57) ABSTRACT

A system, method and apparatus for managing a patient affected with a disease. In one aspect, the invention is directed to an apparatus for managing a patient, the apparatus comprising a system that provides: A) a means for enrolling a patient into a system including storing general information about the patient into the system's database; B) a means for storing a schedule for the patient; C) a means for reminding the patient to execute the patient care activities; D) a means for retrieving patient information comprising responses to side effects questionnaires and laboratory results; E) a means for storing the patient information into the system; F) a means for analyzing the patient information and generating a recommendation; G) a means for submitting the recommendation to a provider for approval; and H) a means for receiving approval or a modified recommendation and sending the recommendation or modified recommendation to the patient.

23 Claims, 4 Drawing Sheets

SYSTEM AND METHOD FOR MANAGING A PATIENT WITH CHRONIC DISEASE

CROSS-REFERENCE TO RELATED APPLICATION

The present application claims the benefit under 35 U.S.C. §119(e) of U.S. Provisional Patent Application Ser. No. 60/615,666, filed on Oct. 4, 2004, entitled "System for Automating Management of Chronic Hepatitis C Virus Patients," which is incorporated herein by reference.

BACKGROUND OF THE INVENTION

Chronic diseases affect around 20% of the U.S. population, which amounts to nearly 90 million U.S. residents. Medical care for persons suffering from chronic diseases accounts for over 70% of total medical care expenditures. One growing chronic disease is Hepatitis C Virus (HCV) with an estimated 4 million cases in the U.S. These numbers are projected to triple in the next 10-20 years with a projected $10.7 billion dollars spent on direct medical expenditures in the United States.

The medical therapies for chronic diseases are cumbersome and typically involve the use of combined pharmacological therapy with associated adverse reactions, frequent dose adjustments and extensive care and monitoring of the patient. In addition to cost of the medications, chronic disease management requires long term, on-going and frequent time commitments primarily of professionally trained staff.

The relatively frequent and serious adverse drug reactions associated with HCV pharmacological therapy makes the management of this disease even more complex and expensive. HCV patients require frequent interventions and a high level of support. Consequently, treatment fails 25-50% of the time. An estimated 30 % of the treatment failure can be ascribed to non-compliance and lack of nursing and medical support. In fact, it has been estimated that the lifetime cost per patient with untreated chronic HCV is around $53,000 for outpatient and hospital care. While a course of potentially curative therapy is approximately $12,000.

Thus, an automated disease management program designed to facilitate chronic medical therapy is of paramount importance today. By decreasing cost and streamlining human resources, such a program eliminates many of the issues described above.

SUMMARY

The invention features systems and methods for consolidating and automating the necessary patient care activities performed by various medical staff members.

Certain aspects of the present disclosure are directed to systems and methods for managing a patient. In one exemplary embodiment, the automated system develops a schedule for the patient, wherein the schedule determines an execution date for patient care activities. Based on the schedule, the system reminds the patient or a third party to execute the patient care activities, which results in the generation of patient information. The system retrieves and stores the patient information into the system. After analyzing the patient information, the system generates a recommendation based on the patient information thus analyzed. The system sends the recommendation to the provider and the patient for review, approval or modification. The foregoing process may be iterated multiple times, for example, throughout the entire treatment of the patient. In some embodiments, system retrieves a modified recommendation from the provider, where the provider rejects the recommendation thus submitted. The system sends the modified recommendation to the patient.

In various embodiments, the recommendation is of critical status, which results in the notification being sent to the provider in real-time. In another embodiment, the disclosed systems and methods answer questions that patients may have about the management of the disease. To this end, the system receives a question on disease management from the patient and matches the question with a pre-determined answer. If no match is found, then the system contacts the provider with the question and retrieves the answer from the provider. The system responds to the patient with the pre-determined answer and the provider assisted answer.

Further features and advantages of the instant disclosed methods and systems will become more apparent from the following Drawings, Definitions, Detailed Description and Claims.

DEFINITIONS

For convenience, the meaning of certain terms and phrases employed in the detailed description and claims are provided below. Unless defined otherwise, all technical and scientific terms used herein have the same meaning as commonly understood by one of ordinary skill in the art.

| TERM | DEFINITION |
| --- | --- |
| critical status | Patient information that requires immediate attention by a provider. |
| dosage recommendation | The amount of medication prescribed to a patient. |
| entity | A person including, but not limited to, a patient, a provider or a third party. More than one entity may be involved in a process, in which case the entities, which may be of the same or different type are referred to as entity 1, entity 2, etc . . . |
| execution date | The scheduled date for executing or performing a patient care activity. Certain activities may have reoccurring execution dates, such as once every week. |

-continued

| TERM | DEFINITION |
| --- | --- |
| intervention instruction | An adjusted treatment instruction that is aimed at ameliorating side effects, and detecting and preventing potential adverse outcomes from an administered therapy. |
| test | A test conducted by a laboratory or clinic on information obtained from a patient that indicates symptoms and side effects. |
| medical history information | A collection of information concerning the patient's past and current health. This includes, but is not limited to, a list of previous illnesses, present conditions, symptoms, medications and health risk factors. |
| modified recommendation | A recommendation which has been modified by a provider. |
| patient | A person who suffers from a disease, an injury or condition. |
| patient information | Medical information about the patient, including but not limited to, the patient's medical history, reaction (side effects) profile to certain drugs, reported symptoms and side effects, test results, dosage recommendations, and treatment instructions. |
| patient care activities | Actions taken by a patient or third party to treat a disease or a side effect. Examples include, but are not limited to undergoing tests, visiting a provider for a follow-up check, or answering a weekly questionnaire on side effects. |
| provider | A healthcare professional who provides healthcare services to a patient, including but not limited to a physician, a physician's assistant, and an advanced practiced registered nurse. |
| question on disease management | A question being asked by a patient or a third party regarding the disease, the symptoms, the side effects, the dosage recommendations, the treatment recommendations, the intervention instructions, and the administration of any patient care activity. |
| recommendation | An instruction to the patient about the execution of a patient care activity, such as providing the dosage amount for the drug, adjusting the dosage schedule, instructions on the administration of the treatment, providing an intervention for minimizing side effects, recommending more tests. |
| rule | A pre-determined set of algorithms for evaluating patient information. For example, a rule may represent the thought processes that a provider undergoes in evaluating and ameliorating side effects in a patient. |
| schedule | Dates for various patient care activities, such as routine follow-up visits, tests, injections of the drug therapy, and phone calls asking the patient to answer a questionnaire of side effects. |
| side effect | A reaction that is experienced by a patient and is associated with a particular drug or therapy, including but not limited to chest pains, depression, weight loss, diarrhea. |
| side effect questionnaire | A patient interview which reviews symptoms and side effects experienced by the patient. |
| symptom | Any sensation or change in bodily function that is experienced by a patient and is associated with a particular disease. |
| therapy | Any measure taken to treat a disease, including but not limited to the administration of drugs. |

DETAILED DESCRIPTION

Figure 1:
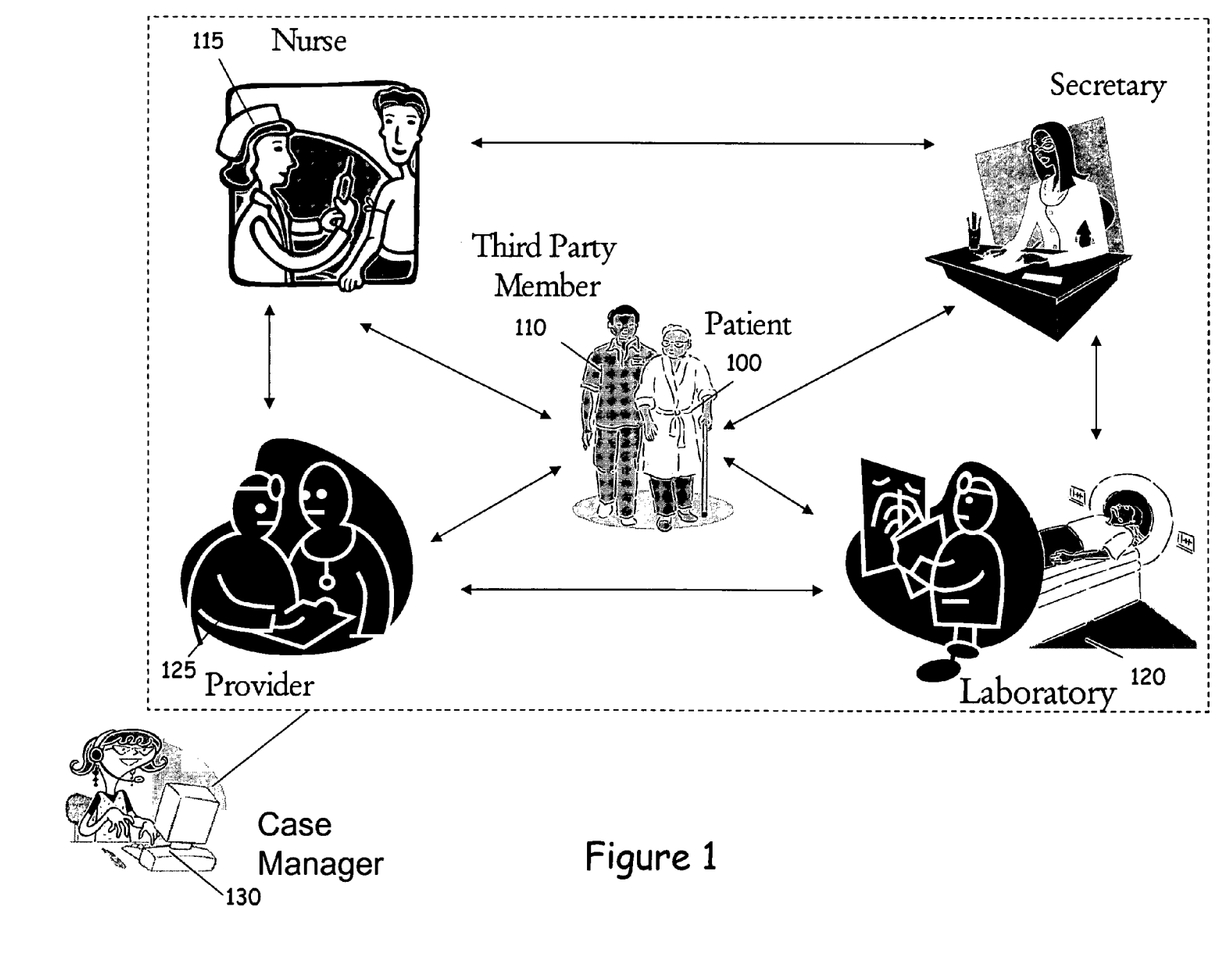
FIG. 1 provides an overview of a traditional patient management team.

FIG. 1 illustrates a traditional team for managing a patient 100 affected by a disease. The patient 100 receives a form of therapy to treat the disease and undergoes periodic tests in order to monitor her symptoms and side effects.

For example, a patient affected with the hepatitis C virus (HCV) receives weekly injections of the drug peginterferon and daily doses of oral anti-viral medications, such as ribavirin. She must have blood work done initially every two weeks in order to monitor her symptoms and side effects. The therapy may cause the patient to suffer from low white blood cell count (or leukopenia) and/or low immature white blood cell count (or neutropenia), both of which increase the patient's risk for infection. She also may suffer from low red blood cell count (or anemia), which results in weakness, shortness of breath, and various cardiac symptoms. Thrombocytopenia (or low platelet count) is another side effect of the therapy that increases the risk of bleeding. Thus, the severity and frequency of the side effects demand frequent monitoring of the patient's laboratory values and symptoms. Other side effects from using peginterferon may include depression, rash, fever, coughing and other flu-like symptoms.

Typically, patient 100 self-administers the therapy at home. In some instances, a third party member 110, such as a family member or a home health nurse, administers the therapy. A nursing staff 115 from the clinic usually educates patient 100 and/or third party member 110, about the proper administration of the therapy. Nursing staff 115 is also responsible for the education about the disease itself, the treatments and the potential side effects. Any need for continued or re-education is done by nursing staff 115 either in the clinic or over telephone.

In order to monitor her symptoms and side effects, patient 100 is required to have tests conducted at the clinic or laboratory 120. The results from the test are sent to provider 125 for review. Provider 125 may be a physician, a physicians' assistant and an advanced practice registered nurse. After provider 125 reviews the laboratory results, she or one of her staff members relays the results to patient 100 either via telephone, e-mail or in person. Provider 125 may contact patient 100 in order to adjust or discontinue the therapy based on the laboratory results and the patient's medical history.

The urgency of the information usually dictates how quickly patient 100 is contacted.

In addition to testing for laboratory values, provider 125 also monitors the patient's various symptoms, or reactions to the therapy. Generally, provider 125 learns of these symptoms during routine follow-up visits or routine phone interviews with the patients. In the case of severe side effects, patient 100 may call nursing staff 115 or provider 125 before scheduling a follow-up visit. Based on these reported symptoms, provider 125 may adjust the dosage and/or discontinue the treatment.

Provider 125 may prescribe adjunct therapies to treat some of the symptoms as well. For example, in the example described above, a provider may prescribe erthropoietin to in order to treat for anemia in the patient; or she may prescribe filgrastim for treating leucopenia/neutropenia in the patient. In cases where adjunct therapies are prescribed, the patient's laboratory values are monitored more frequently than usual. Dosage adjustments for the adjunct therapies are based on the laboratory values, the side effects and the past medical history of the patient.

Figure 2:
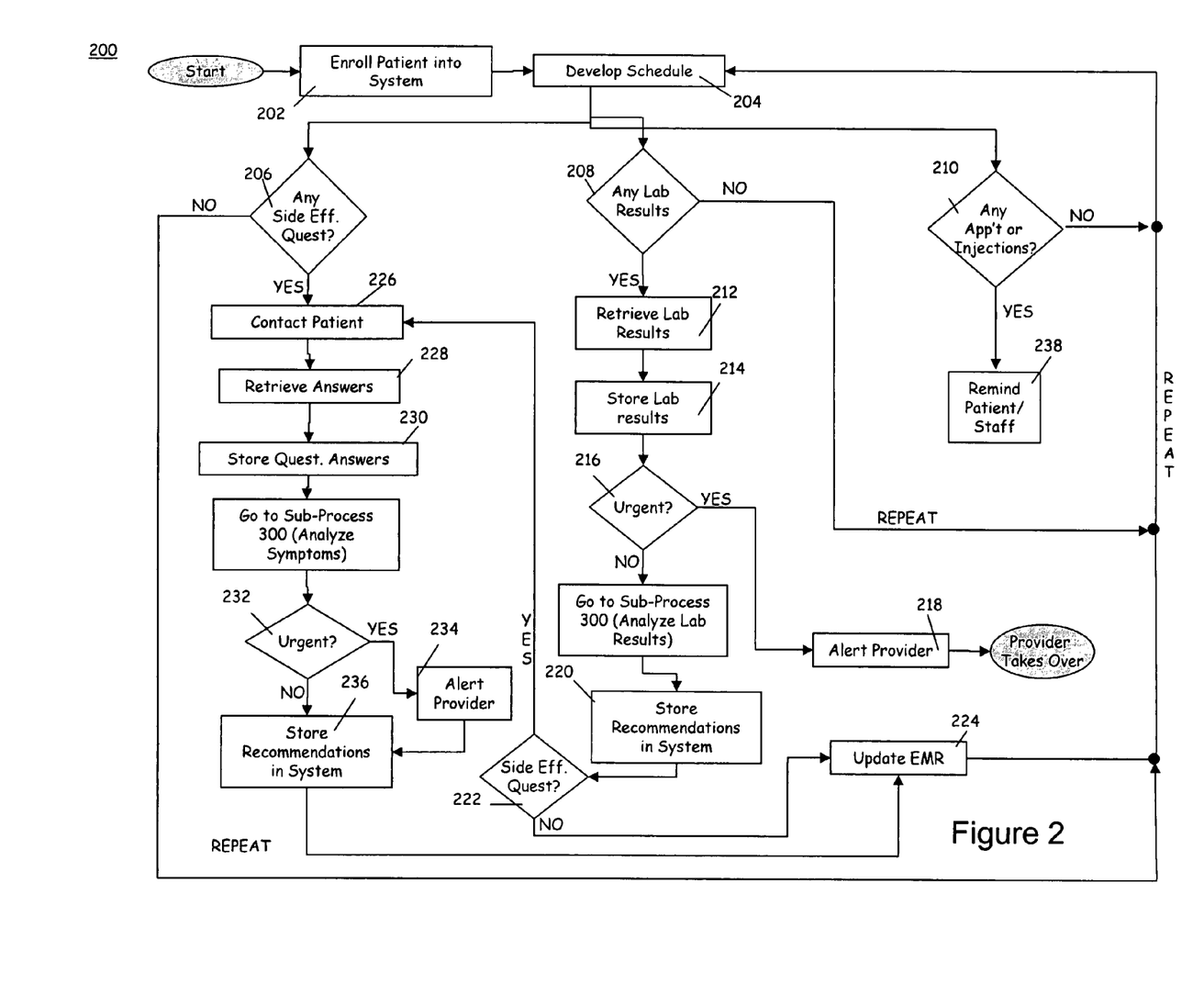
FIG. 2 is a flow diagram of a system for managing a patient with chronic disease.

FIG. 1 also depicts a case manager 130 who coordinates all aspects of the patient's care. As such, the case manager 130 interacts with all members of the management team. As seen above, a need arises for an inexpensive and efficient system for managing patients with chronic diseases. FIG. 2 is a flow diagram of process 200, which automates the management steps.

As shown in FIG. 2, process 200 enrolls (202) a patient with a chronic disease into the system. During the enrollment process (202), information about the patient, as well as information about the provider, medical staff, laboratory facility and pharmacy are stored into the system's database. Patient information may include, but is not limited to medical history, contact information, family history, and allergic reactions. Likewise, laboratory information may include whether an electronic interface exists for the facility. An electronic interface enables a laboratory facility to send the results directly to the system. Where no electronic interface exists, a system for manually inputting the results must be established. In addition, contact information for each of the parties is established during enrollment (202). In particular, each provider is asked to specify her preferred method of external communication, e.g. pager, cellular phone, facsimile and short message service. This ensures that the system can effectively deliver an urgent message to the provider in the event of an emergency.

After enrolling (202) the patient, process 200 develops (204) a schedule for routine laboratory work, periodic patient contacts for side effect profile questionnaires, and regular injections and appointments. Throughout the patient's entire treatment course, process 200 repeatedly inquires (206, 208, 210) whether information is available for each of these schedule events, respectively. At any given point in time, a patient may respond affirmatively or negatively to all or some of the inquires. For example, she may have both laboratory results and a schedule side effects questionnaire simultaneously; or she may have only laboratory results, but no schedule side effects questionnaire.

In one embodiment, process 200 determines (208) whether any laboratory results, such as blood work or urine samples, are available for processing. If laboratory results are available, process 200 retrieves (212) and stores (214) the laboratory results into the system.

Process 200 determines (216) whether the laboratory results require an urgent alert to provider 125. For example, in the case of critically abnormal lab values, process 200 immediately alerts (218) provider 125, in real-time, with an urgent message. Using a decision tree capable of intelligently triaging each alert, process 200 alerts (218) the appropriate medical staff member with the urgent results. As described above, the system has asked each provider, in advance, to specify her preferred method of external communication. After alerting (218) the provider, process 200 allows provider 125 to take over the situation.

Figure 3:
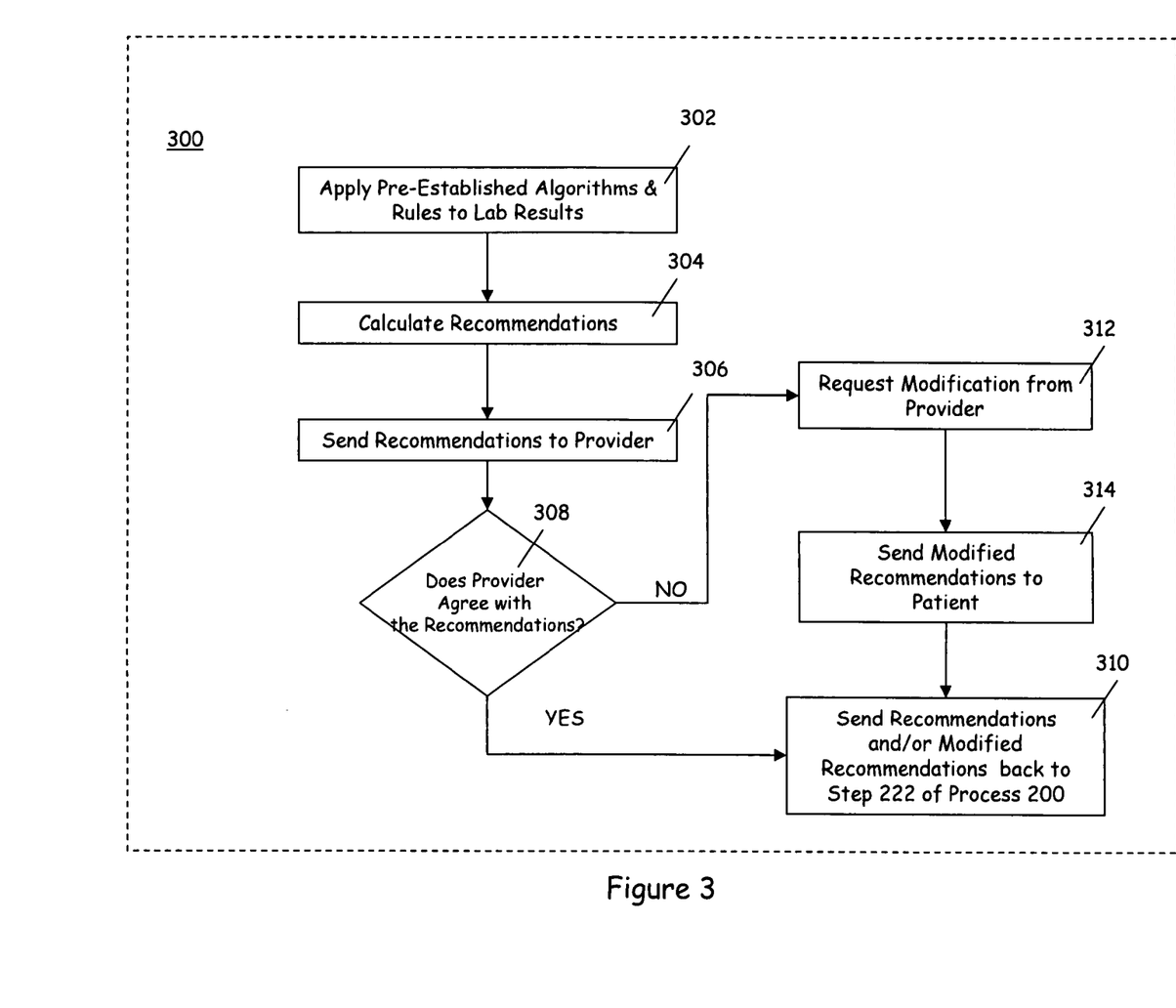
FIG. 3 is a flow diagram of a process for analyzing symptoms and generating recommendations.

For non-urgent laboratory results, process 200 sends the laboratory results to subprocess 300, which analyzes the laboratory results and generates recommendations based on the results.

As shown in FIG. 3, sub-process 300 applies (302) a pre-established set of algorithms and rules to the laboratory results, and calculates (304) recommendations, or dosage adjustments and intervention instructions, based on the laboratory results. The guidelines for these dose adjustments are established by the pharmaceutical companies and medical organizations that recommend the standards of care. Some examples include the National Institute of Health (NIH) and American Association for the Study of Liver Disease (AASLD).

Sub-process 300 submits (306) the recommendations to the provider 125 and inquires (308) whether the provider approves of the recommendation. Upon the provider's approval, the recommendations are sent (314) to the patient 100 and then submitted (310) back to process 200. However, where the provider rejects the recommendation, subprocess 300 requests (312) that the provider modify the recommendations and then submits (314) the modified recommendations to the patient 100 and then sends (310) the recommendations back to process 200.

Referring back to FIG. 2., process 200 stores (220) the recommendations and/or modified recommendations from sub-process 300 into the system. Process 200 then inquires (222) whether a side effect questionnaire is due for the patient. The side effect questionnaire describes the symptoms experienced by patient 100 while using the therapy. The frequency at which the side effect questionnaire is requested differs for each patient. For example, a patient using both the therapy and various adjunct therapies may require a weekly monitor, whereas a patient suffering from a mild form of the disease may require only a monthly monitor.

Where no side effect questionnaire is scheduled at that particular time, process 200 updates (224) the electronic medical record that is stored in the system with the new lab results, symptoms, dosage adjustments and intervention instructions. Throughout the entire treatment course, process 200 is repeated as often as deemed necessary by provider 125.

However, if process 200 determines (222) that a side effect questionnaire is available for patient 100, then process 200 contacts (226) the patient with questions from a side effects questionnaire. The side effects questionnaire contains specific questions directed at analyzing the patient's various symptoms. The questions are specific to management of the disease and the patient's co-morbidities. This side effects questionnaire is modeled after typical questions asked by providers during routine follow-up visits, thus each questionnaire may vary depending on the particular provider taking care of the patient. After patient 100 responds to questionnaire, process 200 retrieves (228) the questionnaire and stores (230) the information into the system.

Figure 4:
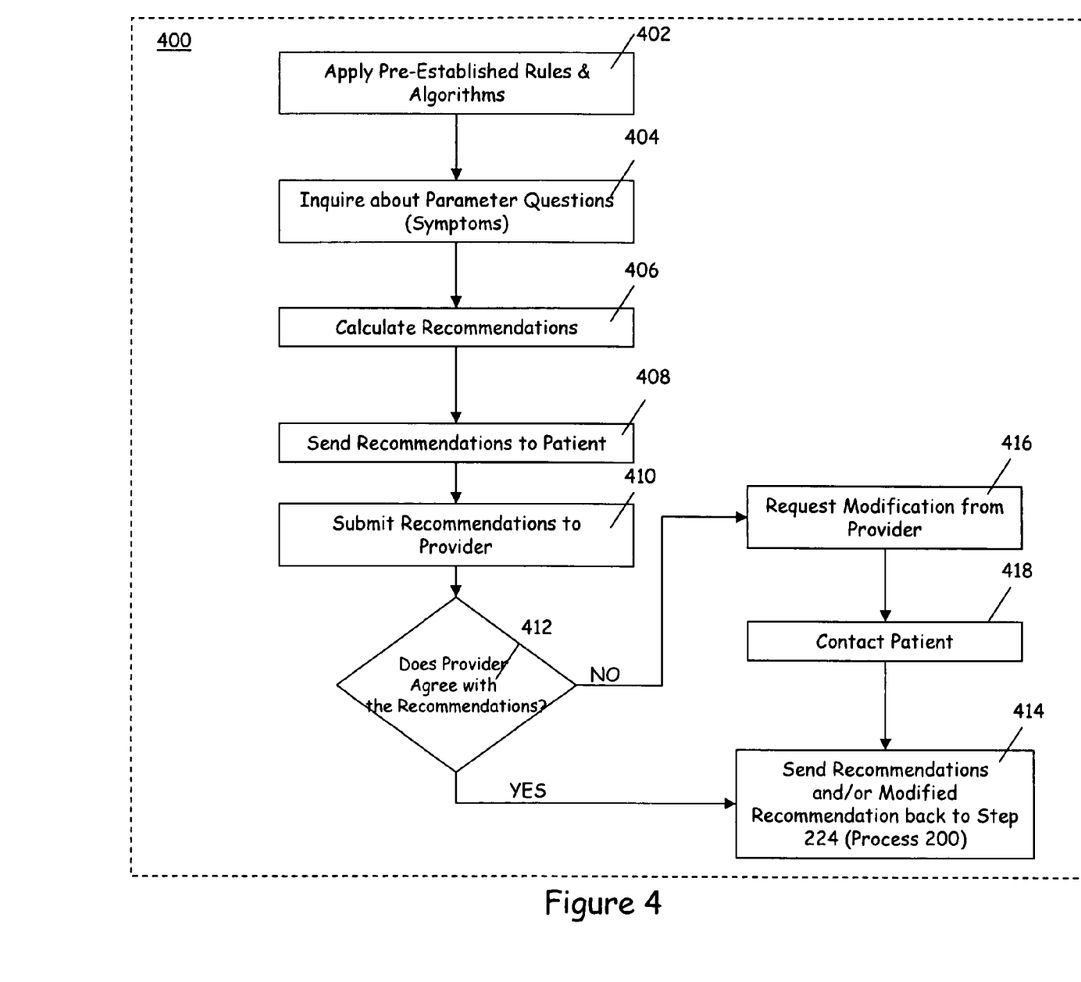
FIG. 4 is a flow diagram of a process for analyzing laboratory results and generating recommendations.

Process 200 then forwards the questionnaire answers to sub-process 400, which analyzes and generates recommendations based on the patient's symptoms. FIG. 4 illustrates sub-process 400, which applies (402) a pre-established set of algorithms and rules to the patient's various symptoms. Each known symptom of the therapy is assigned a particular predetermined algorithm. For example, in the case of the drug peg interferon, which is used for the treatment of HCV, some common side effects include chest pains, depression and anemia. As detailed below, each of these symptoms is analyzed according to a particular set of algorithms.

Sub-process 400 applies (402) the appropriate algorithm by inquiring (404) into the specifics of the symptoms, i.e. parameter questions. For example, a patient may indicate that she is suffering from weight loss and/or anorexia (or the abnormal loss of appetite for food). As a result, sub-process 300 inquires (404) as to the amount of weight lost, e.g. greater than 10%, between 5% and 10%, or less than 5%. Based on these responses to these questions, sub-process 400 then calculates (406) the recommended dosage adjustments and intervention instructions for the patient. Sub-process 400 sends (408) the recommendations to patient 100.

In another embodiment, a patient may experience chest pains. Here, sub-process 400 inquires (404) as to the severity of the pain on a scale from 1 to 10. A selection of a number from 1 to 4 indicates mild pain, whereas a selection of a number from 5 to 7 and 8 to 10 indicates, respectively, moderate and severe pain. Sub-process 300 also inquiries (404) about various coronary artery disease (CAD) factors, as well as the patient's age and gender. In addition, sub-process 400 may inquire (404) as to external reactions such as anemia, infections and fevers. Based on these responses to these questions, sub-process 400 determines (406) the recommended dosage adjustments and intervention instructions for the patient. Sub-process 400 then sends (408) the recommendations back to patient 100.

Sub-process 400 may be applied to any number of symptoms, including but not limited to nausea, vomiting, diarrhea, depression, dyspnea/coughing, aggression, irritability, visual changes, and other flu-like symptoms.

After submission (408) of the recommendations to patient 100, sub-process 400 sends (410) the recommendations to the provider 125 and inquires (412) whether the provider approves of the recommendation. Upon the provider's approval, sub-process 400 coordinates the modified recommendations with the recommendations based on the laboratory results, and submits (414) the coordinate recommendations back to process 200.

Where the provider does not approve of the recommendation, sub-process 400 requests (416) that the provider modify the recommendations. The provider may contact (418) the patient 100 about these modifications by either calling patient 100 directly, or leaving a message for patient 100 on the system. Sub-process 400 reconciles the modified recommendations from sub-process 400 with the recommendations derived from sub-process 300, and submits (414) the reconciled recommendations back to process 200.

Referring back to FIG. 2, process 200 determines (232) whether the recommendations require an urgent alert to provider 125. As described above, if process 200 detects an urgent message, it alerts (234) the appropriate medical staff member with the results. As described above, the system has asked each provider, in advance, to specify her preferred method of external communication. After alerting (234) the provider, process 200 stores (236) the recommendations into the system. Process 200 updates (224) the electronic medical record that is stored in the system with the new lab results, symptoms, dosage adjustments and intervention instructions. Throughout the entire treatment course, process 200 is repeated as often as deemed necessary by provider 125.

Process 200 also determines (210) whether patient 100 has an upcoming follow-up visit, a laboratory appointment or a scheduled therapy injection. Process 200 sends (238) reminder notifications regarding each of these appointments to patients 100. Reminder notifications may also be sent (238) to medical staff in order to remind them of pending items. In the preferred embodiment, the system notifies each patient in her preferred language, e.g. English, Spanish, Creole or Chinese.

In addition, process 200 may determine the adequacy of the patient's medical supply. The system contains information regarding the pharmacies used by the patient, provider and clinic. If a refill is deemed necessary, process 200 generates a refill request and sends the refill request directly to the pharmacy for further processing. In some embodiments, process 200 generates and submits laboratory and/or radiology requests to corresponding imaging and radiology departments as well.

At any point during process 200, patient 100 may contact the system in order to listen to instructions, learn about lab results, report a new side effect (in advance of a scheduled profile questionnaire request), report a medication refill or record an ad lib message. In addition, patient 100 may obtain educational information regarding various aspects of the treatment, such as the disease, therapy, proper administration of the drugs, proven complimentary therapies, medications and medication side effects by contacting the system as well. A pre-determined set of answers addressing commonly asked questions is available to patient 100 through the system. Questions that cannot be handled by the system are forwarded to an appropriate medical staff member. The staff member may record on the system a response to the patient's query, which is then relayed to the patient.

In some embodiments, the system incorporates a round-the-clock system maintenance, redundancy and surveillance in order to quickly identify any malfunctions. In the case of a malfunction, the patient's care team is alerted immediately, and the care team resumes any direct patient care.

Equivalents

The methods and systems described herein are not limited to the specific formats set forth above. Elements of different implementations may be combined to form other implementations not specifically described above. Other implementations not specifically described herein, may be ascertain by those of skill in the art using no more than routine experimentation and are within the scope of the following claims.

Although the present invention has been described in the context of HCV treatment, various other chronic diseases, such as HIV and diabetes, may be treated by the system as well. For example, the system may monitor a cohort of patients using a study drug, which requires frequent checking of adverse drug reactions and patient status. In another example, the system monitors patients on chemotherapy and require close monitoring of her symptoms and laboratory values.

What is claimed is:

1. A computer program product, tangibly embodied in a computer readable storage medium, the computer program product being operable to cause a data processing apparatus, in a network of interconnected computers to:
   A) enroll a patient into a system by storing general information about the patient comprising medical history, reaction to drugs, symptoms and side effects, test results, contact information and family history into the system's database;
   B) prompt a provider to specify a preferred method of external communication;
   C) develop a schedule of patient care activities that is specific to the patient comprising routine laboratory work, side effects questionnaires and regular injections and appointments wherein the side effects questionnaires comprise asking the patient questions related to the patient's symptoms and side effects;

D) repeatedly inquire whether information including laboratory results and responses to the side effects questionnaires are available for processing;

E) optionally remind an entity of scheduled patient care activities;

F) retrieve and store patient information comprising the responses to the side effects questionnaires and the laboratory results;

G) analyze the patient information by applying a set of algorithms to the patient information;

H) generate a recommendation based on the analysis in step G) comprising a dosage adjustment, instructions on an administration of a treatment, advising for more tests and an intervention instruction wherein the intervention instruction is an adjusted treatment instruction aimed at ameliorating side effects and detecting and preventing potential adverse outcomes from an administered therapy;

I) submit the recommendation to the patient directly and/or to the provider for an approval or a modified recommendation; and J) receive the approval of the recommendation or the modified recommendation from the provider and send the recommendation or the modified recommendation to the patient.

2. The computer program product of claim 1, wherein in step H) the recommendation is marked as critical status and the patient information is sent to the provider in real-time using the provider's preferred method of external communication.

3. The computer program product of claim 1, wherein laboratory information including whether a laboratory facility has an electronic interface to communicate with the system is stored in the system's database.

4. The computer program product of claim 1, wherein a frequency at which the side effects questionnaires are scheduled depends upon the patient's needs.

5. The computer program product of claim 1, wherein the side effects questionnaires ask questions specific to the patient's disease and to the patient's symptoms.

6. The computer program product of claim 1, which is further able to receive a question from the patient, match the question with a stored answer when the stored answer exists and forward the question to an appropriate medical staff member when the stored answer does not exist.

7. The computer program product of claim 1, wherein the entity is selected from the group consisting of the patient, the provider and a third-party.

8. The computer program product of claim 1, which is accessible via a network.

9. The computer program product of claim 8, wherein the network is the internet.

10. An apparatus for managing a patient, the apparatus comprising a system that provides:

A) a means for enrolling a patient by storing general information about the patient comprising medical history, reaction to drugs, symptoms and side effects, test results, contact information and family history into a database;

B) a means for developing and storing a schedule for the patient, wherein the schedule determines an execution date for a plurality of patient care activities comprising routine laboratory work, symptoms and side effects questionnaires and regular injections and appointments;

C) a means for reminding an entity to execute the patient care activities;

D) a means for retrieving patient information comprising responses to the symptoms and side effects questionnaires and laboratory results;

E) a means for storing the patient information into the system;

F) a means for analyzing the patient information by applying a set of algorithms to the patient information;

G) a means for generating a recommendation on an output from the analyzing means wherein the recommendation comprises a dosage adjustment, instructions on an administration of a treatment, advising for more tests and an intervention instruction;

H) a means for submitting the recommendation directly to the patient and/or to a provider for an approval;

I) a means for receiving the approval of the recommendation or a modified recommendation from the provider; and J) a means for sending the approval or the modified recommendation to the patient.

11. The apparatus of claim 10, wherein the recommendation is marked as critical status and the patient information is sent to the provider in real-time.

12. The apparatus of claim 10, further comprising a means for determining whether a laboratory facility has an electronic interface to communicate with the system.

13. The apparatus of claim 10, which further provides a means to receive a question from the patient and match the question with a stored answer when the stored answer exists and forward the question to the provider when the stored answer does not exist.

14. The apparatus of claim 10, wherein the entity is selected from the group consisting of the patient, the provider and a third-party.

15. The apparatus of claim 10, which includes a network.

16. The apparatus of claim 10, wherein the network is the internet.

17. The computer program of claim 1, wherein the side effects questionnaires are modeled after questions asked by the provider during routine follow-up visits.

18. The computer program of claim 1, wherein the system determines whether the patient needs a medication refill and if so, generates and sends a refill request directly to a pharmacy.

19. The computer program of claim 6, which is further able to receive an answer to the patient's question from the medical staff member, stored the answer to the patient's question on the system, and provide the patient access to the answer.

20. A computer program product, tangibly embodied in a computer readable storage medium, the computer program product being operable to cause a data processing apparatus, in a network of interconnected computers to:

A) enroll a patient into a system by storing general information about the patient comprising medical history, reaction to drugs, symptoms and side effects, test results, contact information and family history into a database;

B) prompt a provider to specify a preferred method of external communication;

C) develop a schedule of patient care activities comprising routine laboratory work, side effects questionnaires, regular injections and appointments;

D) retrieve and store the patient's laboratory results;

E) analyze the laboratory results by applying a first set of algorithms to the laboratory results;

F) generate a first recommendation for a first dosage adjustment or a first intervention instruction based on the analysis in step E);
G) submit the first recommendation to the provider for approval or a first modified recommendation;
H) receive the approval of the first recommendation or the first modified recommendation from the provider and send the first recommendation or the first modified recommendation to the database;
I) contact the patient with questions from the side effects questionnaires;
J) retrieve and store responses to the side effects questionnaires;
K) analyze the responses to the side effects questionnaires by applying a second set of algorithms to the responses to the side effects questionnaires;
L) generate a second recommendation for a second dosage adjustment or a second intervention instruction based on the analysis in step K);
M) submit the second recommendation directly to the patient;
N) submit the second recommendation to the provider for approval or a second modified recommendation;
O) receive the approval of the second recommendation or the second modified recommendation from the provider; and
P) reconcile the first recommendation or the first modified recommendation with the second recommendation or the second modified recommendation to derive a coordinated recommendation and submit the coordinated recommendation to the system and to the patient.

21. The computer program product of claim 5, wherein the provider can modify, add or delete questions asked in the side effects questionnaires.

22. The computer program product of claim 1, wherein a question asked in the side effects questionnaires is dependent upon a response to a previous question.

23. The computer program product of claim 1, wherein step A) further includes storing information about the provider, a medical staff, a laboratory facility and a pharmacy in the database.

* * * * *